(12) United States Patent
Collins et al.

(10) Patent No.: US 7,476,547 B2
(45) Date of Patent: *Jan. 13, 2009

(54) CELL SEPARATION COMPOSITIONS AND METHODS

(75) Inventors: Daniel P. Collins, Lino Lakes, MN (US); David M. Shaut, Woodbury, MN (US); Joel H. Hapke, Brooklyn Center, MN (US)

(73) Assignee: BioE, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/564,148

(22) Filed: Nov. 28, 2006

(65) Prior Publication Data

US 2007/0154961 A1 Jul. 5, 2007

Related U.S. Application Data

(62) Division of application No. 10/094,456, filed on Mar. 7, 2002, now Pat. No. 7,160,723.

(60) Provisional application No. 60/282,823, filed on Apr. 10, 2001.

(51) Int. Cl.
   *G01N 1/18* (2006.01)
(52) U.S. Cl. .................. 436/177; 435/2; 435/7.23; 435/7.24; 435/7.25; 435/355; 435/372.2; 435/372.3; 436/523; 436/529; 436/10; 436/17; 436/63; 436/64; 424/93.71
(58) Field of Classification Search .............. 435/7.2, 435/7.21, 7.23, 7.24, 7.25, 40.5, 40.52, 326, 435/328, 343, 343.1, 343.2, 344, 344.1, 366, 435/374, 384.1, 7.5, 2, 372.1, 372.2, 372.3; 436/514, 518, 523, 529, 547, 548, 10, 16, 436/17, 18, 63, 64, 166, 176, 177, 179; 204/183.2; 210/678, 806, 781, 782, 793; 530/387.7, 530/388.1, 388.8, 391.1
See application file for complete search history.

(56) References Cited

U.S. PATENT DOCUMENTS

| | | | |
|---|---|---|---|
| 4,946,778 A | | 8/1990 | Ladner et al. |
| 5,773,224 A | * | 6/1998 | Grandics et al. ............. 435/7.2 |
| 5,840,502 A | * | 11/1998 | Van Vlasselaer ........... 435/7.21 |
| 5,877,299 A | | 3/1999 | Thomas et al. |
| 6,048,715 A | | 4/2000 | Haynes et al. |
| 6,117,985 A | | 9/2000 | Thomas et al. |
| 6,146,628 A | | 11/2000 | Uckun et al. |
| 6,153,113 A | | 11/2000 | Goodrich et al. |
| 6,280,622 B1 | * | 8/2001 | Goodrich et al. ............ 210/252 |
| 6,448,075 B1 | | 9/2002 | Thomas et al. |
| 6,491,917 B1 | * | 12/2002 | Thomas et al. ........... 424/140.1 |
| 6,544,751 B1 | * | 4/2003 | Brandwein et al. ........... 435/7.1 |
| 6,933,148 B2 | * | 8/2005 | Collins et al. ............... 435/372 |
| 7,135,335 B2 | | 11/2006 | Thomas et al. |
| 7,160,723 B2 | | 1/2007 | Collins et al. |
| 2005/0132444 A1 | | 6/2005 | Xu |

FOREIGN PATENT DOCUMENTS

| | | |
|---|---|---|
| CA | 2 279 474 | 7/1998 |
| EP | 0 670 185 | 9/1995 |
| EP | 0 844 482 | 5/1998 |
| JP | 10/059854 | 3/1998 |
| WO | WO 02/83262 | 10/2002 |
| WO | WO 04/29208 | 4/2004 |

OTHER PUBLICATIONS

U.S. Appl. No. 11/627,762, filed Jan. 2007, Collins et al.*
Cruse et al. (Illustrated Dictionary of Immunology, CRC Press Inc 1995, pp. 157-159).*
Bigbee et al., "Monoclonal Antibodies Specific for the M- and N-Forms of Human Glycoprotein A," *Mol. Immunol.*, 1983, 20(12): 1353-1362.
Cole et al., "The EBV-Hybridoma Technique and its Application to Human Lung Cancer," *Monoclonal Antibodies and Cancer Therapy*, 1985, Alan R. Liss, Inc., New York, pp. 77-96.
Cote et al., "Generation of human monoclonal antibodies reactive with cellular antigens," *Proc. Natl. Acad. Sci. USA*, 1983, 80:2026-2030.
Collins, "Cytokine and cytokine receptor expression as a biological indicator of immune activation: important considerations in the development of in vitro model systems," *J. Immunol. Meth.*, 2000, 243:125-145.
Eggens et al., "Specific Interaction between Lex and Lex Determinants," *J. Biol. Chem.*, 1989, 264(16):9476-9484.
Huse et al., "Generation of a Large Combinatorial Library of the Immunoglobulin Repertoire in Phage Lambda," *Science*, 1989, 246:1275-1281.
Jennings et al., "CD9 cluster workshop report: cell surface binding and functional analysis," *Leucocyte Typing V*, 1995, Oxford University Press, Oxford, pp. 1249-1251.
Kannagi et al., "A Series of Human Erythrocyte Glycosphingolipids Reacting to the Monoclonal Antibody Directed to a Developmentally Regulated Antigen, SSEA-1," *J. Biol. Chem.*, 1982, 257(2):14865-14872.
Kishimoto(chairman), *6th International Workshop and Conference on Human Leukocyte Differentiation Antigens*, Nov. 10-14, 1996, Kobe, Japan (Table of Contents Only).
Knapp et al. (eds.), *Leukocyte Typing IV*, 1989, Oxford University Press, Oxford (Table of Contents Only).
Kohler and Milstein, "Continuous cultures of fused cells secreting antibody of predefined specificity," *Nature*, 1975, 256(5512):495-497.

(Continued)

*Primary Examiner*—Gailene R Gabel
(74) *Attorney, Agent, or Firm*—Fish & Richardson P.C.

(57) ABSTRACT

The invention provides compositions and methods for cell separation. These reagents and techniques specifically agglutinate cells via surface antigen recognition and can be used to recover even rare cell types in high yield.

8 Claims, No Drawings

OTHER PUBLICATIONS

Kozbor and Roder, "The production of monoclonal antibodies from human lymphocytes," *Immunol. Today*, 1983, 4(3):72-79.

Lanza et al., "cDNA Cloning and Expression of Platelet p24/CD9," *J. Biol. Chem.*, 1991, 266(16):10638-10645.

Magnani et al., "Monoclonal Antibodies PMN 6, PMN 29, and PM-81 Bind Differently to Glycolipids Containing a Sugar Sequence Occurring in Lacto-N-Fucopentaose III," *Arch. Biochem. Biophys.*, 1984, 233(2):501-506.

Outram et al., "Erythromyeloid Lineage Fidelity is Conserved in Erythroleukaemia," *Leukemia Research*, 1988, 12(8):651-657.

Reinherz et al. (eds.), *Leukocyte Typing II*, 1986, Springer-Verlag, New York (Table of Contents Only).

Rubinstein et al., "Anti-Platelet Antibody Interactions with Fcγ Receptor," *Seminars in Thrombosis and Hemostasis*, 1995, 21:10-22.

Solter and Knowles, "Monoclonal antibody defining a stage-specific mouse embryonic antigen (SSEA-1)," *Proc. Natl. Acad. Sci. USA*, 1978, 75(11):5565-5569.

Telen and Bolk, "Human red cell antigens," *Transfusion*, 1987, 27:309-314.

Vanderlaan et al., "Monoclonal antibodies specific for the M- and N-forms of human glycophorin A," *Mol. Immunol.*, 1983, 20:1353.

Vettese-Dadey, "Going Their Separate Ways: A Profile of Products for Cell Separation," *The Scientist*, 1999, vol. 13, 10 pages.

Von dem Borne and Modderman, "Cluster Report: CD9," *Leukocyte Typing IV*, 1989, Oxford University Press, Oxford, pp. 989-992.

Wagner, "Umbilical Cord Blood Stem Cell Transplantation," *Am. J. Ped. Hematol./Oncol.*, 1993, 15(2):169-174.

Wright and Tomlinson, "The ins and outs of the transmembrane 4 superfamily," *Immunology Today*, 1994, 15(12):588-594.

Examiner's First Report in Australian Patent Application 2002255678 dated Jul. 27, 2006, 2 pages.

First Office Action in Chinese Patent Application 02808016.5 dated Jun. 9, 2006, 14 pages.

First Examination Report in EP Application No. 02 725 093.5 dated Oct. 5, 2005, 5 pages.

Second Examination Report in EP Application No. 02 725 093.5 dated Mar. 16, 2006, 5 pages.

Third Examination Report in EP Application No. 02 725 093.5 dated Jun. 16, 2006, 5 pages.

First Examination Report in Israel Application No. 158,171 dated Apr. 20, 2007, 4 pages.

First Examination in Report in Indian Application No. 01570/DELNP/2003 dated Jun. 25, 2007, 2 pages.

Official Action in Russian Application No. 2003132547 dated Feb. 9, 2006, 6 pages.

Office Action in Russian Application No. 2003132547 dated Apr. 21, 2006, 5 pages.

First Office Action in China Application No. 03825336.4 dated Dec. 1, 2006, 12 pages.

Examination Report in EU Application No. 03 759 533.7 dated Apr. 4, 2006, 4 pages.

First Examination Report in Indian Application No. 1351/DELNP/2005 dated Dec. 19, 2006, 2 pages.

Office Action in Russian Application No. 2005112731 dated Jun. 25, 2007, 4 pages.

\* cited by examiner

CELL SEPARATION COMPOSITIONS AND METHODS

CROSS-REFERENCE TO RELATED APPLICATIONS

This application is a divisional (and claims the benefit of priority under 35 U.S.C. §120) of U.S. application Ser. No. 10/094,456, filed Mar. 7, 2002, now U.S. Pat. No. 7,160,723, which claims the benefit of U.S. provisional application 60/282,823, filed Apr. 10, 2001. The disclosures of the prior applications are considered part of (and are incorporated by reference in) the disclosure of this application.

TECHNICAL FIELD

The present invention relates to compositions and methods for separating cells.

BACKGROUND

Many conventional blood cell isolation procedures include a preliminary bulk separation of erythrocytic and granulocytic components by density-gradient sedimentation. Density-gradient separation relies on small differences in the density of different cell types causing them to segregate at different levels in a fluid medium of variable density. Differences in density between the cell types can be small, and individual cells types can be heterogeneous in size and density. Consequently, particular cell types can become distributed throughout a density-gradient medium rather than precisely segregating at a discrete area in the density medium. This phenomenon can result in poor recovery of desired cells and/or contamination with undesired cell types. In procedures that enrich for rare blood cell types such as hematopoietic progenitor cells, density-gradient sedimentation generally results in poor yields. For example, using conventional density-gradient methods to isolate progenitor cells (e.g., CD34+ hematopoietic stem cells) from umbilical cord blood reportedly results in a significant loss of the desired stem cells. See e.g., Wagner, J. E., Am J Ped Hematol Oncol 15:169 (1993). As another example, using conventional density-gradient methods to isolate lymphocytes reportedly results in selective loss of particular lymphocyte subsets. See e.g., Collins, D. P., J Immunol Methods 243:125 (2000).

Increasing the recovery of rare cell types from donor tissue could dramatically improve the success of transplant and immune therapies (e.g., bone marrow transplants, stem cell-based gene therapy, and immune cell therapy), the success of which apparently is related to the actual number of the cells being used for therapy.

SUMMARY

The invention provides compositions and methods for separating cells. The disclosed compositions and methods can be used, for example, to efficiently prepare cells for tissue culture, immunophenotypic characterization, other diagnostic testing, further purification, and therapeutic administration.

Methods of the invention involve for contacting a blood cell-containing sample (e.g., peripheral blood sample, umbilical cord sample, and bone marrow sample) with a cell separation composition. Without being bound by a particular mechanism, compositions of the invention can selectively agglutinate cells via interaction with cell surface antigens and/or by stimulating cell-cell adherence (e.g., via increased expression of cell surface adhesion factors). Agglutinated cells partition away from unagglutinated cells, which remain in solution. Cells can be recovered from either or both the agglutinate or the supernatant phase.

The disclosed compositions and methods can be used to isolate and enrich for a variety of cell types, including, for example, T lymphocytes, T helper cells, T suppressor cells, B cells, hematopoietic stem cells, circulating embryonic stem cells, circulating fetal cells in maternal circulation, and circulating metastatic tumor cells. The disclosed compositions and methods can be used in the context of allogenic and autologous transplantation. In the context of autologous transplantation, the disclosed compositions and methods can be used, for example, to remove undesired cells such as metastatic cancer cells from a patient's blood or bone marrow. Desirable cells (e.g., hematopoietic stem cells) then can be returned back to a patient without, or substantially free of, life-threatening tumor cells. The disclosed compositions and methods can be applied to cells of any mammal, including humans, non-human primates, rodents, swine, bovines and equines.

Cell separation compositions can contain dextran, anti-glycophorin A antibody, as well as antibodies against cell surface antigens such as CD9, CD15, CD2, CD3, CD4, CD8, CD72, CD16, CD41a, HLA Class 1, HLA-DR, CD29, CD11a, CD11b, CD11c, CD19, CD20, CD23, CD39, CD40, CD43, CD44, CDw49d, CD53, CD54, CD62L, CD63, CD66, CD67, CD81, CD82, CD99, CD100, Leu-13, TPA-1, or surface Ig, and combinations thereof. Cell separation compositions can contain antibodies against surface antigens of other types of cells (e.g., cell surface proteins of tumor cells).

Antibodies against cell surface antigens can be included in a cell separation composition in either or both soluble and substrate-bound forms. Antibodies can be bound to substrates such as latex microparticles, acid-etched glass particles, aggregated polypeptides, polysaccharides, avidin particles, or biotinylated agarose gel particles. Antibodies in cell separation compositions can be monoclonal and can be IgM or IgG antibodies. In some embodiments, a cell separation contains anrihuman antibody. The concentration of a soluble antibody in a cell separation composition can be about 0.1 mg/l to about 15 mg/l. Substrate-bound antibodies can be included in a cell separation composition at a concentration between about 0.1 and about $50.0 \times 10^9$ particles/l.

Cell separation compositions also can contain heparin, divalent cations (e.g., $Ca^{+2}$, $Mg^{+2}$), and phosphate buffered saline. In some embodiments, compositions have a pH between 6.8 to 7.8 (e.g., between 7.2 to 7.4).

The invention also provides kits containing components of a cell separation composition and packaging material. Kits can include a blood collection vessel such as a blood bag or a vacuum tube.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention features compositions and methods for separating cells. Compositions of the invention can be used to selectively agglutinate cells from blood cell-containing samples. Without being bound by a particular mechanism, compositions of the invention can agglutinate cells via interaction with cell surface antigens and/or by stimulating expression of cell surface adhesion factors such as LFA-1 (Lymphocyte Function-Associated Antigen-1, CD11a/CD18) and ICAM-1 (Intercellular Adhesion Molecule-1, CD54). Agglutinated cells partition away from unagglutinated cells, which remain in solution. Cells can be recovered from the supernatant or from the agglutinate.

Cell Separation Compositions

A cell separation composition in accord with the invention can contain dextran and one or more antibodies against (i.e., that have specific binding affinity for) a cell surface antigen.

Dextran is a polysaccharide consisting of glucose units linked predominantly in alpha (1 to 6) mode. Dextran can cause stacking of erythrocytes (i.e., rouleau formation) and thereby facilitate the removal of erythroid cells from solution. Antibodies against cell surface antigens can facilitate the removal of blood cells from solution via homotypic agglutination (i.e., agglutination of cells of the same cell type) and/or heterotypic agglutination (i.e., agglutination of cells of different cell types).

Cell separation compositions can contain antibodies against blood cell surface antigens including, for example, glycophorin A, CD15, CD9, CD2, CD3, CD4, CD8, CD72, CD16, CD41a, HLA Class I, HLA-DR, CD29, CD11a, CD11b, CD11c, CD19, CD20, CD23, CD39, CD40, CD43, CD44, CDw49d, CD53, CD54, CD62L, CD63, CD66, CD67, CD81, CD82, CD99, CD100, Leu-13, TPA-1, surface Ig, and combinations thereof. Thus, cell separation compositions can be formulated to selectively agglutinate particular types of blood cells.

In some embodiments, a cell separation composition includes antibodies against glycophorin A. Anti-glycophorin A antibodies can facilitate the removal of red cells from solution by at least two mechanisms. First, anti-glycophorin A antibodies can cause homotypic agglutination of erythrocytes since glycophorin A is the major surface glycoprotein on erythrocytes. In addition, anti-glycophorin A antibodies also can stabilize dextran-mediated rouleau formation. Exemplary monoclonal anti-glycophorin A antibodies include, without limitation, 107FMN (Murine IgG1 Isotype), YTH89.1 (Rat IgG2b Isotype), and E4 (Murine IgM Isotype). See e.g., M. Vanderlaan et al., Molecular Immunology 20:1353 (1983); Telen M. J. and Bolk, T. A., Transfusion 27: 309 (1987); and Outram S. et al., Leukocyte Research. 12:651 (1988).

In some embodiments, a cell separation composition includes antibodies against CD15. Anti-CD15 antibodies can cause homotypic agglutination of granulocytes by crosslinking CD15 molecules that are present on the surface of granulocytes. Anti CD15 antibodies also can cause homotypic and heterotypic agglutination of granulocytes with monocytes, NK-cells and B-cells by stimulating expression of adhesion molecules (e.g., L-selectin and beta-2 integrin) on the surface of granulocytes that interact with adhesion molecules on monocytes, NK-cells and B-cells. Heterotypic agglutination of these cell types can facilitate the removal of these cells from solution along with red cell components. Exemplary monoclonal anti-CD15 antibodies include, without limitation, AHN1.1 (Murine IgM Isotype), FMC-10 (Murine IgM Isotype), BU-28 (Murine IgM Isotype), MEM-157 (Murine IgM Isotype), MEM-158 (Murine IgM Isotype), MEM-167 (Murine IgM Isotype). See e.g., *Leukocyte typing IV* (1989); *Leukocyte typing II* (1984); *Leukocyte typing VI* (1995); Solter D. et al., Proceedings of National Academy of Sciences USA 75:5565 (1978); Kannagi R. et al., Journal of Biological Chemistry 257:14865 (1982); Magnani, J. L. et al., Archives of Biochemistry and Biophysics 233:501 (1984); Eggens I. et al., Journal of Biological Chemistry 264:9476 (1989).

In some embodiments, a cell separation composition includes antibodies against CD9. Anti-CD9 antibodies can cause homotypic agglutination of platelets. Anti-CD9 antibodies also can cause heterotypic agglutination of granulocytes and monocytes via platelets that have adhered to the surface of granulocytes and monocytes. CD9 antibodies can promote the expression of platelet 1-selectin, which facilitates the binding of platelets to leukocyte cell surfaces. Thus, anti-CD9 antibodies can promote multiple cell-cell linkages and thereby facilitate agglutination and removal from solution. Exemplary monoclonal anti-CD9 antibodies include, without limitation, MEM-61 (Murine IgG1 Isotype), MEM-62 (Murine IgG1 Isotype), MEM-192 (Murine IgM Isotype), FMC-8 (Murine IgG2a Isotype), SN4 (Murine IgG1 Isotype), BU-16 (Murine IgG2a Isotype). See e.g., *Leukocyte typing VI* (1995); *Leukocyte typing II* (1984); Von dem Bourne A. E. G. Kr. and Moderman P. N. (1989) In *Leukocyte typing IV* (ed. W. Knapp, et al), pp. 989-92. Oxford University Press, Oxford; Jennings, L. K., et al. In *Leukocyte typing V*, ed. S. F. Schlossmann et at., pp. 1249-51. Oxford University Press, Oxford (1995); Lanza F. et al., Journal of Biological Chemistry 266: 10638 (1991); Wright et al., Immunology Today 15:588 (1994); Rubinstein E. et al., Seminars in Thrombosis and Hemostasis 21:10 (1995).

In some embodiments, a cell separation composition contains antibodies against CD41, which can selectively agglutinate platelets. In some embodiments, a cell separation composition contains antibodies against CD3, which can selectively agglutinate T-cells. In some embodiments, a cell separation composition contains antibodies against CD2, which can selectively agglutinate T-cells and NK cells. In some embodiments, a cell separation composition contains antibodies against CD72, which can selectively agglutinate B-cells. In some embodiments, a cell separation composition contains antibodies against CD16, which can selectively agglutinate NK cells and neutrophilic granulocytes.

As mentioned above, cell separation compositions can be formulated to selectively agglutinate particular blood cells. As an example, a cell separation composition containing antibodies against glycophorin A, CD15, and CD9 can facilitate the agglutination of erythrocytes, granulocytes, NK cells, B cells, and platelets. T cells, NK cells and rare precursor cells then can be recovered from solution. If the formulation also contained an antibody against CD3, T cells also could be agglutinated, and NK cells and rare precursors could be recovered from solution.

Cell separation compositions can contain antibodies against surface antigens of other types of cells (e.g., cell surface proteins of tumor cells). Those of skill in the art can use routine methods to prepare antibodies against cell surface antigens of blood, and other, cells from humans and other mammals, including, for example, non-human primates, rodents (e.g., mice, rats, hamsters, rabbits and guinea pigs), swine, bovines, and equines.

Typically, antibodies used in the composition are monoclonal antibodies, which are homogeneous populations of antibodies to a particular epitope contained within an antigen. Suitable monoclonal antibodies are commercially available, or can be prepared using standard hybridoma technology. In particular, monoclonal antibodies can be obtained by techniques that provide for the production of antibody molecules by continuous cell lines in culture, including the technique described by Kohler, G. et al., Nature, 1975, 256:495, the human B-cell hybridoma technique (Kosbor et al., Immunology Today 4:72 (1983); Cole et al., Proc. Natl. Acad. Sci. USA 80:2026 (1983)), and the EBV-hybridoma technique (Cole et al., "Monoclonal Antibodies and Cancer Therapy," Alan R. Liss, Inc., pp. 77-96 (1983)).

Antibodies can be of any immunoglobulin class including IgG, IgM, IgE, IgA, IgD, and any subclass thereof. Antibodies of the IgG and IgM isotypes are particularly useful in cell separation compositions of the invention. Pentameric IgM antibodies contain more antigen binding sites than IgG antibodies and can, in some cases (e.g., anti-glycophorin A and anti-CD15), be particularly useful for cell separation reagents. In other cases (e.g., anti-CD9 antibodies), antibodies of the IgG isotype are particularly useful for stimulating homotypic and/or heterotypic agglutination.

Antibodies against cell surface antigens can be provided in liquid phase (i.e., soluble). Liquid phase antibodies typically are provided in a cell separation composition at a concentration between about 0.1 and about 15 mg/l (e.g., between 0.25 to 10, 0.25 to 1, 0.5 to 2, 1 to 2, 4 to 8, 5 to 10 mg/l).

Antibodies against cell surface antigens also can be provided in association with a solid phase (i.e., substrate-bound). Antibodies against different cell surface antigens can be covalently linked to a solid phase to promote crosslinking of cell surface molecules and activation of cell surface adhesion molecules. The use of substrate-bound antibodies can facilitate cell separation (e.g., by virtue of the mass that the particles contribute to agglutinated cells, or by virtue of properties useful for purification).

In some embodiments, the solid phase with which an substrate-bound antibody is associated is particulate. In some embodiments, an antibody is bound to a latex microparticle such as a paramagnetic bead (e.g., via biotin-avidin linkage, covalent linkage to COO groups on polystyrene beads, or covalent linkage to $NH_2$ groups on modified beads). In some embodiments, an antibody is bound to an acid-etched glass particle (e.g., via biotin-avidin linkage). In some embodiments, an antibody is bound to an aggregated polypeptide such as aggregated bovine serum albumin (e.g., via biotin-avidin linkage, or covalent linkage to polypeptide COO groups or $NH_2$ groups). In some embodiments, an antibody is covalently linked to a polysaccharide such as high molecular weight (e.g., >1,000,000 $M_r$) dextran sulfate. In some embodiments, biotinylated antibodies are linked to avidin particles, creating tetrameric complexes having four antibody molecules per avidin molecule. In some embodiments, antibodies are bound to biotinylated agarose gel particles (One Cell Systems, Cambridge, Mass., U.S.A.) via biotin-avidin-biotinylated antibody linkages. Such particles typically are about 300-500 microns in size, and can be created in a sonicating water bath or in a rapidly mixed water bath.

Cell-substrate particles (i.e., particles including cells and substrate-bound antibodies) can sediment from solution as an agglutinate. Cell-substrate particles also can be removed from solution by, for example, an applied magnetic field, as when the particle is a paramagnetic bead. Substrate-bound antibodies typically are provided in a cell separation composition at a concentration between about 0.1 and about 50.0× $10^9$ particles/l (e.g., between 0.25 to 10.0× $10^9$, 1 to 20.0× $10^9$, 2 to 10.0× $10^9$, 0.5 to 2× $10^9$, 2 to 5× $10^9$, 5 to 10× $10^9$, and 10 to 30× $10^9$ particles/l), where particles refers to solid phase particles having antibodies bound thereto.

Cell separation compositions also can contain divalent cations (e.g., $Ca^{+2}$ and $Mg^{+2}$). Divalent cations can be provided, for example, by a balanced salt solution (e.g., Hank's balanced salt solution). $Ca^{+2}$ ions reportedly are important for selectin-mediated and integrin-mediated cell-cell adherence.

Cell separation compositions of the invention also can contain an anticoagulant such as heparin. Heparin can prevent clotting and non-specific cell loss associated with clotting in a high calcium environment. Heparin also promotes platelet clumping. Clumped platelets can adhere to granulocytes and monocytes and thereby enhance heterotypic agglutination more so than single platelets. Heparin can be supplied as a heparin salt (e.g., sodium heparin, lithium heparin, or potassium heparin).

Cell Searation Methods

The disclosed compositions can be used, for example, to efficiently prepare cells for tissue culture, immunophenotypic characterization, other diagnostic testing, further purification, and therapeutic administration. Without being bound by a particular mechanism, compositions of the invention can selectively agglutinate cells via interaction with cell surface antigens and/or by stimulating cell-cell adherence (e.g., via increased expression of cell surface adhesion factors). Agglutinated cells partition away from unagglutinated cells, which remain in solution.

After agglutination, unagglutinated cells can be recovered from the solution phase. Cells also can be recovered from the agglutinate. Agglutinated cells can be dissociated by, for example, transferring the cells into buffers that contain divalent cation chelators such as EDTA or EGTA. Cells recovered from the agglutinate can be further separated by using antibodies against cell surface antigens. Cells can be recovered from a gel microparticle-antibody-cell agglutinate by heating the agglutinate to a temperature just above the melting point.

The disclosed compositions can be used to separate cells from a variety of samples, including peripheral blood (e.g., obtained by venipuncture), umbilical cord blood (e.g., obtained post-gravida), and bone marrow (e.g., from aspirate). Blood cell-containing samples can be contacted with a cell separation composition to cause agglutination of particular types of cells. For example, erythrocytes and differentiated myeloid blood constituents can be selectively agglutinated using cell separation compositions containing antibodies to surface antigens of these cells. The disclosed compositions and methods can be used to isolate and enrich for a variety of cell types, including, for example, T lymphocytes, T helper cells, T suppressor cells, B cells, hematopoietic stem cells, circulating embryonic stem cells, circulating fetal cells in maternal circulation, and circulating metastatic tumor cells. The disclosed compositions can used to agglutinate cells of any mammal, including humans, non-human primates, rodents, swine, bovines and equines.

The disclosed compositions and methods can be used in the context of allogenic and autologous transplantation. In the context of autologous transplantation, the disclosed compositions and methods can be used, for example, to remove undesired cells such as metastatic cancer cells from a patient's blood or bone marrow. Desirable cells (e.g., hematopoietic stem cells) then can be returned back to a patient without, or substantially free of, life-threatening tumor cells.

Cell separation compositions containing antibodies against cell surface proteins of tumor cells can be used to purge tumor cells from a patient's blood or bone marrow. Such compositions also can be used for diagnostic procedures to, for example, obtain and detect tumor cells in an agglutinate, where they are concentrated and are therefore more easily detectable than in circulating blood or in bone marrow. A cell separation composition containing antibodies against the receptor for epithelial growth factor can be used to agglutinate tumor cells derived from epithelial tumors (e.g., head and neck tumors). A cell separation composition containing antibodies against estrogen receptors can be used to agglutinate tumor cells derived from breast and ovarian tumors. A cell separation composition containing antibodies against surface immunoglobulins can be used to agglutinate tumor cells associated with chronic lymphocytic leukemia, plasmacytoma, and multiple myeloma. Breast carcinoma cells express CD15 on their cell surface, and can be purged from bone marrow using cell separations that contain antibodies against CD15. Other formulas can be made on the basis of cell type and cell surface proteins to obtain or deplete metastatic tumor cells derived from other carcinomas (e.g., erythroleukemia, endothelial carcinoma, and gastrointestinal carcinoma) from a patient's blood or bone marrow.

Cell Separation Kits

A cell separation composition can be combined with packaging material and sold as a kit. The components of a cell separation composition can be packaged individually or in combination with one another. In some embodiments, the packaging material includes a blood collection vessel (e.g., blood bag, vacuum tube). The packaging material included in a kit typically contains instructions or a label describing how the cell separation composition can be used to agglutinate particular types of cells. Components and methods for producing such kits are well known.

The invention is fuirther described in the following examples, which do not limit the scope of the invention described in the claims.

EXAMPLES

Example 1

Separating Blood Cells

This example describes the general method by which cells were separated using the cell separation reagents described below. An equal volume of a cell separation reagent (i.e., 25 ml) was combined with an equal volume of an EDTA anticoagulated heparinized peripheral blood sample (i.e., 25 ml) in a 50 ml conical tube. Samples containing white blood cell counts greater than $20 \times 10^6$ cells/ml were combined one part blood with two parts cell separation reagent. Tubes were gently mixed on a rocker platform for 30 to 45 minutes at room temperature. Tubes were stood upright in a rack for 30 to 50 minutes to permit agglutinated cells to partition away from unagglutinated cells, which remained in solution. Without disturbing the agglutinate, a pipette was used to recover unagglutinated cells from the supernatant. Recovered cells were washed in 25 ml PBS and centrifuged at 500×g for 7 minutes. The cell pellet was resuspended in 4 ml PBS.

Cells also were recovered from the agglutinate using a hypotonic lysing solution containing ethylenediaminetetraacetic acid (EDTA) and ethylene glycol-bis(2-aminoethylether)-N,N,N',N'-tetraacetic acid (EGTA). Agglutinated cells were treated with 25 ml VitaLyse™ (BioErgonomics, St. Paul, Minn.) and vortexed. After 10 minutes, cells either were exposed to an applied magnetic field to recover cells associated with antibodies bound to paramagnetic beads, or were centrifuged at 500×g for 7 minutes and the supernatant was removed. In either case, cells were resuspended in 4 ml PBS.

Recoveries of erythrocytes, leukocytes, lymphocytes, monocytes, granulocytes, T cells, B cells, and NK cells were determined by flow cytometry and immunophenotyping. Prior to flow cytometry, leukocyte recovery (i.e., white blood cell count) was determined using a Coulter Onyx Hematology Analyzer, and samples were adjusted with PBS to a cell count of $1 \times 10^7$ cells/ml. 100 ul aliquots of volume-adjusted sample were stained at room temperature in the dark for 15 to 30 minutes with either FITC labeled anti-CD3 antibodies (reactive to T cells), PE labeled anti-CD19 antibodies (reactive to B cells), or PE labeled anti-CD16 antibodies (reactive to NK cells). 2 ml of PBS was added to each sample, and the sample was then vortexed and centrifuged to pellet cells. Supernatants were discarded, and cell pellets were vortexed and resuspended in 0.5 ml PBS. Stained and unstained cells were analyzed by flow cytometry using a Coulter XL flow cytometer. Erythrocytes, leukocytes, lymphocytes, monocytes, granulocytes and platelets were identified on the basis of diagnostic forward and side light scatter properties. B cells, T cells, and NK cells were identified on the basis of light scattering and staining by labeled antibodies.

Example 2

Erythrocyte Agglutination

The reagent described in Table 1 was used to separate cells according to the method described in Example 1.

TABLE 1

| | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody clone E4) | 1.0 mg/l |

Results of a separation are shown in Table 2. Erythrocytes were depleted 99.7% from the supernatant. Lymphocytes (T cells, B cells, and NK cells) were enriched in the supernatant relative to the monocytes and granulocytes.

TABLE 2

| | Before separation | After separation |
|---|---|---|
| Erythrocytes per ml | $4.41 \times 10^9$ | $0.015 \times 10^9$ |
| Leukocytes per ml | $5.9 \times 10^6$ | $5.3 \times 10^6$ |
| Lymphocytes (%) | 28.7 | 41.9 |
| Monocytes (%) | 8.69 | 4.78 |
| Granulocytes (%) | 62.5 | 52.6 |
| T Cells (CD3+) | 19.7 | 31.8 |
| B Cells (CD19+) | 4.46 | 5.42 |
| NK Cells (CD16+) | 3.15 | 5.9 |

Example 3

Erythrocyte and CD2+ Cell Agglutination

The reagent described in Table 3 was used to separate cells according to the method described in Example 1.

TABLE 3

| | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |

TABLE 3-continued

| | |
|---|---|
| Anti-human glycophorin A (murine IgM monoclonal antibody, clone E4) | 1.0 mg/l |
| Anti-human CD2 paramagnetic agglutination particles (avidin-coated 4.3 micron diameter paramagnetic polystyrene particles labeled with saturating doses of biotin-labeled mouse anti-human CD2, clone d118.10.1) | $14.02 \times 10^9$ particles/l |

Results of a separation are shown in Table 4. In the supernatant, erythrocytes were depleted 99.7%, T cells were depleted 95.1%, and NK cells were depleted 69.1%. B cells were enriched in the supernatant relative to other cells.

TABLE 4

| | Before separation | After separation |
|---|---|---|
| Erythrocytes per ml | $4.41 \times 10^9$ | $0.014 \times 10^9$ |
| Leukocytes per ml | $5.9 \times 10^6$ | $2.63 \times 10^6$ |
| Lymphocytes (%) | 28.7 | 16.0 |
| Monocytes (%) | 8.69 | 6.04 |
| Granulocytes (%) | 62.5 | 75.6 |
| T Cells (CD3+) | 19.7 | 3.3 |
| B Cells (CD19+) | 4.46 | 9.63 |
| NK Cells (CD16+) | 3.15 | 4.32 |

Example 4

Erythrocyte and CD72+ Cell Agglutination

The reagent described in Table 5 was used to separate cells according to the method described in Example 1.

TABLE 5

| | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone E4) | 1.0 mg/l |
| Anti-human CD72 paramagnetic agglutination particles (avidin-coated 4.3 micron diameter paramagnetic polystyrene particles labeled with saturating doses of biotin-labeled mouse anti-human CD72, clone BU40) | $2.63 \times 10^6$ particles/ml |

Results of a separation are shown in Table 6. In the supernatant, erythrocytes were depleted 99.5%, and B cells were depleted 81.6%.

TABLE 6

| | Before separation | After separation |
|---|---|---|
| Erythrocytes per ml | $4.41 \times 10^9$ | $0.021 \times 10^9$ |
| Leukocytes per ml | $5.9 \times 10^6$ | $3.2 \times 10^6$ |
| Lymphocytes (%) | 28.7 | 47.0 |
| Monocytes (%) | 8.69 | 4.78 |
| Granulocytes (%) | 62.5 | 47.7 |
| T Cells (CD3+) | 19.7 | 41.3 |
| B Cells (CD19+) | 4.46 | 2.75 |
| NK Cells (CD16+) | 3.15 | 4.77 |

Example 5

Erythrocyte, CD15+ Cell, and CD9+ Cell Agglutination

The reagent described in Table 7 was used to separate cells according to the method described in Example 1.

TABLE 7

| | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone E4) | 0.1-15 mg/l (preferably about 1.0 mg/l) |
| Anti-CD15 (murine IgM monoclonal antibody, clone MEM-158) | 0.1-15 mg/l (preferably about 1.0 mg/l) |
| Anti-CD9 (murine IgG monoclonal antibody, clone MEM-61) | 0.1-15 mg/l (preferably about 1.0 mg/l) |

Results of a separation are shown in Table 8. In the supernatant, erythrocytes were depleted 99.9%, monocytes and granulocytes were depleted 99.8%, B cells were depleted 74%, and NK cells were depleted 64.9%. In addition, platelets, present in the supernatant at $226 \times 10^6$/ml before separation, were depleted to $1.4 \times 10^6$/ml for 99.4% depletion.

TABLE 8

| | Before separation | After separation |
|---|---|---|
| Erythrocytes per ml | $4.41 \times 10^9$ | $0.006 \times 10^9$ |
| Leukocytes per ml | $5.9 \times 10^6$ | $1.53 \times 10^6$ |
| Lymphocytes (%) | 28.7 | 99.0 |
| Monocytes (%) | 8.69 | 0.12 |
| Granulocytes (%) | 62.5 | .083 |
| T Cells (CD3+) | 19.7 | 83.2 |
| B Cells (CD19+) | 4.46 | 8.10 |
| NK Cells (CD16+) | 3.15 | 8.43 |

Example 6

Erythrocyte, CD15+ Cell, CD9+ Cell, and CD2+ Cell Agglutination

The reagent described in Table 9 was used to separate cells according to the method described in Example 1.

TABLE 9

| | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone E4) | 1 mg/l |
| Anti-CD15 (murine IgM monoclonal antibody, clone MEM-158) | 1 mg/l |
| Anti-CD9 (murine IgG monoclonal antibody, clone MEM-61) | 1 mg/l |
| Anti-human CD2 paramagnetic agglutination particles (avidin-coated 4.3 micron diameter paramagnetic polystyrene particles labeled with saturating doses of biotin-labeled mouse anti-human CD2, clone d118.10.1) | $14.02 \times 10^9$ particles/l |

Results of a separation are shown in Table 10. In the supernatant, erythrocytes were depleted 99.9%, monocytes and granulocytes were depleted 99.9%, B cells were depleted 16.8%, NK cells were depleted 29%, and T cells were depleted 91.5%. In addition, platelets, present in the supernatant at $226 \times 10^6$/ml before separation, were depleted to $0.3 \times 10^6$/ml for 99.9% depletion.

TABLE 10

|  | Before separation | After separation |
| --- | --- | --- |
| Erythrocytes per ml | $4.41 \times 10^9$ | $0.005 \times 10^9$ |
| Leukocytes per ml | $5.9 \times 10^6$ | $1.26 \times 10^6$ |
| Lymphocytes (%) | 28.7 | 99.8 |
| Monocytes (%) | 8.69 | 0.06 |
| Granulocytes (%) | 62.5 | 0.09 |
| T Cells (CD3+) | 19.7 | 6.78 |
| B Cells (CD19+) | 4.46 | 69.5 |
| NK Cells (CD16+) | 3.15 | 20.7 |

Example 7

Erythrocyte, CD15+ Cell, CD9+ Cell, and CD72+ Cell Agglutination

The reagent described in Table 11 was used to separate cells according to the method described in Example 1.

TABLE 11

| | |
| --- | --- |
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone E4) | 1 mg/l |
| Anti-CD15 (murine IgM monoclonal antibody, clone MEM-158) | 1 mg/l |
| Anti-CD9 (murine IgG monoclonal antibody, clone MEM-61) | 1 mg/l |
| Anti-human CD72 paramagnetic agglutination particles (avidin-coated 4.3 micron diameter paramagnetic polystyrene particles labeled with saturating doses of biotin-labeled mouse anti-human CD72, clone BU40) | $2.63 \times 10^9$ particles/l |

Results of a separation are shown in Table 12. In the supernatant, erythrocytes were depleted 99.9%, monocytes were depleted beyond detection, granulocytes were depleted 99.97%, B cells were depleted 97.2%, NK cells were depleted 54.9%. In addition, platelets, present in the supernatant at $226 \times 10^6$/ml before separation, were depleted to $0.1 \times 10^6$/ml for 99.96% depletion.

TABLE 12

|  | Before separation | After separation |
| --- | --- | --- |
| Erythrocytes per ml | $4.41 \times 10^9$ | $0.006 \times 10^9$ |
| Leukocytes per ml | $5.9 \times 10^6$ | $2.3 \times 10^6$ |
| Lymphocytes (%) | 28.7 | 99.9 |
| Monocytes (%) | 8.69 | 0 |
| Granulocytes (%) | 62.5 | 0.1 |
| T Cells (CD3+) | 19.7 | 92.4 |
| B Cells (CD19+) | 4.46 | 0.59 |
| NK Cells (CD16+) | 3.15 | 7.02 |

Example 8

Erythrocyte, CD15+ Cell, CD9+ Cell, CD19+ Cell, and CD16+ Cell Agglutination

The reagent described in Table 13 was used to separate cells according to the method described in Example 1. T cells and CD3+ cells were recovered from the supernatant. B cells and granulocytes are recovered from the agglutinate.

TABLE 13

| | |
| --- | --- |
| Dextran (average molecular weight 413,000) | 20 g/l |
| Dulbecco's phosphate buffered saline (10X) | 100 ml/l |
| Hank's balanced salt solution (pH 7.2-7.4) | 50 ml/l |
| Sodium Heparin (10,000 units/ml) | 1 ml/l |
| Anti-human glycophorin A (murine IgM monoclonal antibody, clone E4) | 0.1-15 mg/l (preferably about 1.0 mg/l) |
| Anti-human CD15 (murine IgM monoclonal antibody, clone MEM-158) | 0.1-15 mg/l (preferably about 1.0 mg/l) |
| Anti-human CD9 (murine IgM monoclonal antibody, clone MEM-61) | 0.1-15 mg/l (preferably about 1.0 mg/l) |
| Anti-CD19 paramagnetic agglutination particles (avidin-coated 4.3 micron diameter paramagnetic polystyrene particles labeled with saturating doses of biotin-labeled mouse anti-human CD19, clone HIB19) | $0.1$-$30.0 \times 10^9$ particles/l (preferably about $19.8 \times 10^9$ particles/l) |
| Anti-CD16 paramagnetic agglutination particles (avidin-coated 4.3 micron diameter paramagnetic polystyrene particles labeled with saturating doses of biotin-labeled mouse anti-human CD16, clone 3G8) | $5.5 \times 10^{11}$ particles/l |

Example 9

Erythrocyte, CD15+ Cell, CD9+ Cell, CD19+ Cell, CD16+ Cell, and CD4+ Cell Agglutination The reagent described in Table 14 was used to separate cells according to the method described in Example 1. CD8+ cells were recovered from the supernatant.

TABLE 14

| | |
| --- | --- |
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone E4) | 0.1-15 mg/l (preferably about 1.0 mg/l) |
| Anti-human CD15 (murine IgM monoclonal antibody, clone MEM-158) | 0.1-15 mg/l (preferably about 1.0 mg/l) |
| Anti-human CD9 (murine IgM monoclonal antibody, clone MEM-61) | 0.1-15 mg/l (preferably about 1.0 mg/l) |
| Anti-CD19 paramagnetic agglutination particles (avidin-coated 4.3 micron diameter paramagnetic polystyrene particles labeled with saturating doses of biotin-labeled mouse anti-human CD19, clone HIB19) | $0.1$-$30.0 \times 10^9$ particles/l (preferably about $19.8 \times 10^9$ particles/l) |
| Anti-CD16 paramagnetic agglutination particles (avidin-coated 4.3 micron diameter paramagnetic polystyrene particles labeled with saturating doses of biotin-labeled mouse anti-human CD16, clone 3G8) | $5.5 \times 10^{11}$ particles/l |
| Anti-CD4 paramagnetic agglutination particles (avidin-coated 4.3 micron diameter paramagnetic polystyrene particles labeled with saturating doses of biotin-labeled mouse anti-human CD4, clone RFT4-γ or clone QS4120) | $1.2 \times 10^{10}$ particles/l |

Example 10

Erythrocyte, CD15+ Cell, CD9+ Cell, CD19+ Cell, CD16+ Cell, and CD8+ Cell Agglutination The reagent described in Table 15 is used to separate cells according to the method described in Example 1. CD4+ cells are recovered from the supernatant.

TABLE 15

| | |
|---|---|
| Dextran (Average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal Antibody) clone E4 | 0.1-15 mg/l (preferably about 1.0 mg/l) |
| Anti-human CD15 (murine IgM monoclonal Antibody) (clone MEM-158) | 0.1-15 mg/l (preferably about 1.0 mg/l) |
| Anti-human CD9 (murine IgM monoclonal antibody) (clone MEM-61) | 0.1-15 mg/l (preferably about 1.0 mg/l) |
| Anti-CD19 agglutination particles (avidin-coated 4.3 micron diameter paramagnetic polystyrene particles labeled with saturating doses of biotin-labeled mouse anti-human CD19 (clone HIB19) | $0.1\text{-}30.0 \times 10^9$ particles/l (preferably about $19.8 \times 10^9$ particles/l) |
| Anti-CD16 agglutination particle (avidin-coated 4.3 micron diameter paramagnetic polystyrene particles labeled with saturating doses of biotin-labeled mouse anti-human CD16 (clone 3G8) | $5.5 \times 10^{11}$ particles/l |
| Anti-CD8 agglutination particle (avidin-coated 4.3 micron diameter paramagnetic polystyrene particles labeled with saturating doses of biotin-labeled mouse anti-human CD8 (clone HIT8a) | $7.92 \times 10^9$ particles/l |

Example 11

Erythrocyte, CD15+ Cell, CD9+ Cell, CD19+ Cell, and CD2+ Cell Agglutination

The reagent described in Table 16 was used to separate cells according to the method described in Example 1. CD34+ cells were recovered from the supernatant at >50% purity and >80% yield.

TABLE 16

| | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone E4) | 0.1-15 mg/l (preferably about 1.0 mg/l) |
| Anti-human CD15 (murine IgM monoclonal antibody, clone MEM-158) | 0.1-15 mg/l (preferably about 1.0 mg/l) |
| Anti-human CD9 (murine IgM monoclonal antibody, clone MEM-61) | 0.1-15 mg/l (preferably about 1.0 mg/l) |
| Anti-CD19 agglutination particles (avidin-coated 4.3 micron diameter paramagnetic polystyrene particles labeled with saturating doses of biotin-labeled mouse anti-human CD19, clone HIB19) | $0.1\text{-}30.0 \times 10^9$ particles/l (preferably about $19.8 \times 10^9$ particles/l) |
| Anti-CD2 agglutination particles (avidin-coated 4.3 micron diameter paramagnetic polystyrene particles labeled with saturating doses of biotin-labeled mouse anti-human CD2, clone d118.10.1) | $0.1\text{-}30.0 \times 10^9$ particles/l (preferably about $3.0 \times 10^{10}$ particles/l) |

Example 12

Erythrocyte, CD15+ Cell, CD9+ Cell, CD2+ Cell, and CD16+ Cell Agglutination

The reagent described in Table 17 was used to separate cells according to the method described in Example 1. B cells were recovered from the supernatant.

TABLE 17

| | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone E4) | 0.1-15 mg/l (preferably about 1.0 mg/l) |
| Anti-human CD15 (murine IgM monoclonal antibody, clone MEM-158) | 0.1-15 mg/l (preferably about 1.0 mg/l) |
| Anti-human CD9 (murine IgM monoclonal antibody, clone MEM-61) | 0.1-15 mg/l (preferably about 1.0 mg/l) |
| Anti-CD2 agglutination particles (avidin-coated 4.3 micron diameter paramagnetic polystyrene particles labeled with saturating doses of biotin-labeled mouse anti-human CD2, clone d118.10.I) | $0.1\text{-}30.0 \times 10^9$ particles/l (preferably about $3.0 \times 10^{10}$ particles/l) |
| Anti-CD16 agglutination particles (avidin-coated 4.3 micron diameter paramagnetic polystyrene particles labeled with saturating doses of biotin-labeled mouse anti-human CD16, clone 3G8) | $5.5 \times 10^{11}$ particles/l |

OTHER EMBODIMENTS

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A method for separating cells, said method comprising:
   a) contacting a blood cell-containing sample with a composition, said composition comprising:
      i) soluble dextran;
      ii) anti-glycophorin A antibody;
      iii) anti-CD15 antibody; and
      iv) anti-CD9 antibody, wherein said anti-glycophorin A antibody, said anti-CD 15 antibody, and said anti-CD9 antibody are in solution;
   b) allowing said sample to partition into an agglutinate phase and a supernatant phase; and
   c) recovering said cells from said agglutinate phase or said supernatant phase.

2. The method of claim 1, wherein said sample is derived from a human.

3. The method of claim 2, wherein said sample is a peripheral blood sample.

4. The method of claim 2, wherein said sample is an umbilical cord sample.

5. The method of claim 2, wherein said sample is a bone marrow sample.

6. The method of claim 2, wherein said cells are metastatic tumor cells.

7. The method of claim 2, wherein said cells are recovered from said supernatant phase.

8. The method of claim 7, wherein said cells are stem cells.

* * * * *